US010982049B2

(12) United States Patent
Watanabe et al.

(10) Patent No.: US 10,982,049 B2
(45) Date of Patent: Apr. 20, 2021

(54) POLYARYLENE SULFIDE RESIN AND MANUFACTURING METHOD THEREFOR, POLY(ARYLENE SULFONIUM SALT) AND MANUFACTURING METHOD THEREFOR, AND SULFOXIDE

(71) Applicants: DIC Corporation, Tokyo (JP); National University Corporation, Iwate University, Morioka (JP)

(72) Inventors: Hajime Watanabe, Ichihara (JP); Takashi Furusawa, Ichihara (JP); Satoshi Ogawa, Morioka (JP); Toshikazu Takata, Tokyo (JP)

(73) Assignees: DIC Corporation, Tokyo (JP); National University Corporation, Iwate University, Morioka (JP)

( * ) Notice: Subject to any disclaimer, the term of this patent is extended or adjusted under 35 U.S.C. 154(b) by 0 days.

(21) Appl. No.: 16/446,104

(22) Filed: Jun. 19, 2019

(65) Prior Publication Data
US 2019/0300652 A1 Oct. 3, 2019

Related U.S. Application Data

(60) Continuation of application No. 15/484,599, filed on Apr. 11, 2017, now Pat. No. 10,385,168, which is a division of application No. 14/915,974, filed as application No. PCT/JP2014/073088 on Sep. 2, 2014, now Pat. No. 9,657,142.

(30) Foreign Application Priority Data

Sep. 3, 2013 (JP) ................. 2013-182603

(51) Int. Cl.
C08G 75/02 (2016.01)
C08G 75/14 (2006.01)
C07C 321/30 (2006.01)
C07C 317/22 (2006.01)
C07C 323/65 (2006.01)
C08G 75/0286 (2016.01)
C08G 75/12 (2016.01)

(52) U.S. Cl.
CPC ........ *C08G 75/0272* (2013.01); *C07C 317/22* (2013.01); *C07C 321/30* (2013.01); *C07C 323/65* (2013.01); *C08G 75/0286* (2013.01); *C08G 75/12* (2013.01); *C08G 75/14* (2013.01)

(58) Field of Classification Search
CPC .... C07F 7/0801; C07F 7/0832; C07F 7/0827; C08G 75/00; C07B 51/00; C07D 209/12
See application file for complete search history.

(56) References Cited

U.S. PATENT DOCUMENTS 2,513,188 A   6/1950   Macallum
2,583,941 A   1/1952   Gordon, Jr.
3,432,468 A   3/1969   Gabler
3,532,677 A   10/1970  Baron
3,987,016 A   10/1976  Haddad et al.
4,772,679 A   9/1988   Fukawa et al.
5,480,568 A   1/1996   Pawloski et al.

FOREIGN PATENT DOCUMENTS

| DE | 2403660 A1 | 8/1974 |
| DE | 3941494 A1 | 6/1990 |
| EP | 0409496 A2 | 1/1991 |
| EP | 0623640 A1 | 11/1994 |
| GB | 1402314 A | 8/1975 |
| JP | 45-019713 B | 7/1970 |
| JP | S62-091530 A | 4/1987 |
| JP | H0477587 A | 3/1992 |
| JP | H04283234 A | 10/1992 |
| JP | 05-032780 A | 2/1993 |
| JP | 05-148363 A | 6/1993 |
| JP | 05-178993 A | 7/1993 |
| JP | 07-003024 A | 1/1995 |
| JP | 09-048854 A | 2/1997 |
| JP | 10-182823 A | 7/1998 |
| JP | 2008-120956 A | 5/2008 |
| JP | 2011-241299 A | 12/2011 |
| JP | 2013-515848 A | 5/2013 |
| WO | 2011/082197 A1 | 7/2011 |

OTHER PUBLICATIONS

Kenji Kobayashi et al., "Remote Pummerer Reaction via Intermolecular Through-Space Interaction between Sulfonium and Sulfenyl Sulfur Atoms", Journal of Organic Chemistry, vol. 64, 1999, pp. 3190-3195.

Kenichi Oyaizu et al., "Convenient Syntheses of Methylsulfonioarylene and Thioarylene Polymers from 1, 4-bis (Methylsulfinyl)Obenzene", Journal of Macromolecular Science, Part A: Pure and Applied Chemistry, vol. 40, Issue 4, 2003, pp. 415-423.

Satoshi Ogawa et al., "Synthesis and Properties of Poly(p-phenylene sulfide) Derivatives via Poly(sulfonium salt) by Copolymerization of Two Monomer Species", The 94th Annual Meeting of the Chemical Society of Japan (2014) Proceedings of Lecture, IV, Mar. 12, 2014, p. 1312, information sheets and translation thereof.

(Continued)

*Primary Examiner* — Shane Fang
(74) *Attorney, Agent, or Firm* — Locke Lord LLP; James E. Armstrong, IV; Nicholas J. DiCeglie, Jr.

(57) ABSTRACT

The present invention relates to a method for manufacturing a polyarylene sulfide resin comprising: reacting a sulfoxide represented by the following formula (1) with a particular aromatic compound to obtain a poly(arylenesulfonium salt) having a particular constitutional unit; and dealkylating or dearylating the poly(arylenesulfonium salt) to obtain a polyarylene sulfide resin having a particular constitutional unit,

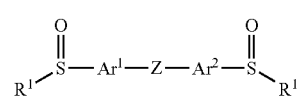

(1)

wherein $R^1$ represents an alkyl group having 1 to 10 carbon atoms, etc.; $Ar^1$ and $Ar^2$ each independently represent an arylene group optionally having a substituent; and Z represents a direct bond, etc.

4 Claims, No Drawings

(56) References Cited

OTHER PUBLICATIONS

International Search Report dated Oct. 28, 2014, issued for PCT/JP2014/073088.

International Preliminary Report on Patentability and Witten Opinion dated Oct. 28, 2014, issued for PCT/JP2014/073088.

Dang T D et al, "Synthesis and characterization of fully disulfonated poly(arylenethioethersulfone)s containing hexafluoroisopropylidene moiety", Polymer, Jan. 21, 2010, pp. 463-468.

Anika Katzfub et al., "Partially Fluorinated sulfonated Poly(arylene sulfone)s Blended with Polybenzimidazole", Journal of Polymer Science Part A Polymer Chemistry, vol. 49, No. 8 , Mar. 2011, pp. 1919-1927.

F. D. Furia et al, "Enantioselective oxidation of thioethers. A route to the resolution of [1,1'-binaphthalene]-2,2'dithiol", Bull Soc Chim Fr, vol. 127, Nov. 1, 1990, pp. 734-744.

L. Dong et al, "Synthesis of 3,3'-substituted biphenyl and binaphthyl-based phosphoramidite ligands", Chinese Journal of Synthetic Chemistry, Chengdu Yuji Huaxuesuo, China vol. 16, No. 6 , Jan. 1, 2008, pp. 656-659.

J. J. Burgi et al, "Unprecedented Selectivity via Electronic Substrate Recognition in the 1,4-Addition to Cyclic Olefins Using a Chiral Disulfoxicle Rhodium Catalyst", Angewandte Chemie International Edition, vol. 48, No. 15, Mar. 3, 2009, pp. 2768-2771.

F. D. Furia et al, "Asymmetric Oxidation of Thioethers. Optical Resolution of [1,1'-Binaphthalene]-2,2'-Dithiol", Tetrahedron Letters vol. 30, Jan. 1, 1989, pp. 2575-2576.

Tobias Seiser et al, "Rhodium(I)-Catalyzed 1,4-Silicon Shift of Unactivated Silanes from Aryl to Alkyl: Enantioselective Synthesis of Indanol Derivatives", Angewandte Chemie International Ed, vol. 49, No. 52, Dec. 27, 2010, pp. 10163-10167.

Supplementary European Search Report dated Apr. 7, 2017, issued for the European patent application No. 14842596.0.

Yong Ding et al., "Novel Synthesis of Poly(thioarylene)s via Reaction between Arenethiols and Bromo Compounds with a Free Radical Initiator," Macromolecules 1997, vol. 30, American Chemical Society, Sep. 22, 1997, pp. 5612-5615.

Office Action dated May 17, 2017, issued for the Chinese patent application No. 201480048468.6.

Office Action issued in corresponding Japanese Patent Application No. JP 2013-182603, dated Oct. 17, 2017.

Office Communication issued in corresponding European Patent Application No. EP 14842596.0 dated Apr. 8, 2019.

In et al., Journal of Polymer Science: Part A: Polymer Chemistry, vol. 44, 2440-2447 (2006).

Ibrahim Haddad et al., "Poly(arylene Sulfides) with Pendant Cyano Groups as High-Temperature Laminating Resins", Journal of Polymer Science, Polymer Chemistry Edition., vol. 11, No. 11, Nov. 1, 1973, pp. 2793-2811. (cited in the Mar. 12, 2020 Search Report issued for EP19210937.9).

European Search Report dated Mar. 12, 2020, issued for the European patent application No. 19210937.9.

POLYARYLENE SULFIDE RESIN AND MANUFACTURING METHOD THEREFOR, POLY(ARYLENE SULFONIUM SALT) AND MANUFACTURING METHOD THEREFOR, AND SULFOXIDE

CROSS REFERENCE TO RELATED APPLICATIONS

This Application is a Continuation of U.S. patent application Ser. No. 15/484,599 filed on Apr. 11, 2017, which Application is a Divisional of U.S. patent application Ser. No. 14/915,974 filed on Mar. 2, 2016, which Application is a 371 U.S. National Phase Application of International PCT Patent Application No. PCT/JP2014/073088, filed Sep. 2, 2014, which application claims priority to Japanese Patent Application No. JP 2013-182603 filed on Sep. 3, 2013. The entire contents of these applications are incorporated herein by reference in their entirety.

TECHNICAL FIELD

The present invention relates to a polyarylene sulfide resin and a manufacturing method therefor, a poly(arylenesulfonium salt) and a manufacturing method therefor, and a sulfoxide.

BACKGROUND ART

Polyarylene sulfide resins (hereinafter sometimes abbreviated as "PAS resin"), the representative of which is a polyphenylene sulfide resin (hereinafter sometimes abbreviated as "PPS resin"), are excellent in heat resistance, chemical resistance and the like and widely utilized for applications such as electric/electronic parts, automotive parts, water heater parts, fibers and films.

A polyphenylene sulfide resin is conventionally manufactured by solution polymerization in which p-dichlorobenzene, and sodium sulfide, or sodium hydrosulfide and sodium hydroxide are used as raw materials to polymerize in an organic polar solvent (e.g., see Patent Literatures 1, 2). Polyphenylene sulfide resins which are currently commercially available are generally produced by this method.

However, since dichlorobenzene is used as a monomer in the method, the concentration of halogen remaining in the resin after synthesis tends to be high and it is necessary to perform polymerization reaction under a severe environment of high temperature and high pressure/strong alkaline, which requires to use a polymerization vessel in which the wetted part is made of titanium, chromium or zirconium, which is expensive and hard-to-process.

Accordingly is known a method for manufacturing a polyarylene sulfide resin under moderate polymerization conditions without using dichlorobenzene as a polymerizing monomer. For example, Patent Literature 3 discloses a solvent-soluble poly(arylenesulfonium salt) as a precursor for synthesizing a polyarylene sulfide resin. A poly(arylenesulfonium salt) is manufactured by a method in which a sulfoxide having one sulfinyl group (hereinafter sometimes referred to as "monofunctional sulfoxide") such as methyl phenyl sulfoxide is homopolymerized under the presence of an acid (e.g., Patent Literature 3).

CITATION LIST

Patent Literature

Patent Literature 1: U.S. Pat. No. 2,513,188
Patent Literature 2: U.S. Pat. No. 2,583,941
Patent Literature 3: Japanese Unexamined Patent Publication No. H9-178993

Non Patent Literature

Non Patent Literature 1: JOURNAL OF MACROMOLECULAR SCIENCE Part A-Pure and Applied Chemistry, Volume 40, Issue 4, p. 415-423

SUMMARY OF INVENTION

Technical Problem

In the case of a method for manufacturing a polyarylene sulfide resin by homopolymerization of a monofunctional sulfoxide, the constitutional unit which the resin has is determined by the structure of the monofunctional sulfoxide as the raw material. Accordingly, when the constitutional unit which a polyarylene sulfide resin has is to be changed depending on a purpose of use or the like, in many cases a monofunctional sulfoxide as the raw material is designed for the first approach. However, the number of available options for the monofunctional sulfoxide is small and the range in which the constitutional unit of a polyarylene sulfide resin can be changed is substantially very limited.

Non Patent Literature 1 discloses a method in which 1,4-bis(methylsulfinyl)benzene, which is a sulfoxide having two sulfinyl groups (hereinafter sometimes referred to as "bifunctional sulfoxide"), is reacted with various aromatic compounds in the presence of phosphorous pentoxide and trifluoromethanesulfonic acid. According to this method, a wide variety of polyarylene sulfide resins having a sulfide group can be manufactured by changing the aromatic compound. However, it is difficult to obtain a resin having a sufficiently high molecular weight using this method.

Accordingly, it is the object of the invention of the present application to provide a method which enables to manufacture a polyarylene sulfide resin having a high degree of freedom for designing the constitutional unit and further having a sufficiently high molecular weight.

Solution to Problem

The present invention relates to a method for manufacturing a polyarylene sulfide resin comprising: reacting a sulfoxide represented by the following formula (1) with an aromatic compound represented by the following formula (2) to obtain a poly(arylenesulfonium salt) having a constitutional unit represented by the following formula (10); and dealkylating or dearylating the poly(arylenesulfonium salt) to obtain a polyarylene sulfide resin having a constitutional unit represented by the following formula (20):

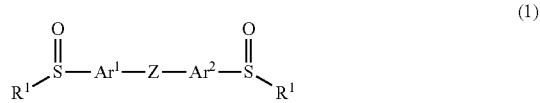

(1)

(2)

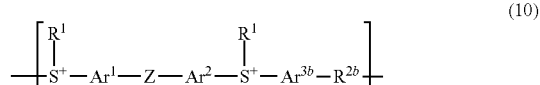

(10)

(20)

wherein in formula (1), (2), (1.0) or (20), $R^1$ represents an alkyl group having 1 to 10 carbon atoms or an aryl group optionally having an alkyl group having 1 to 10 carbon atoms; $R^{2a}$ represents a hydrogen atom, $-Ar^4$, $-S-Ar^4$, $-O-Ar^4$, $-CO-Ar^4$, $-SO_2-Ar^4$ or $-C(CF_3)_2-Ar^4$; $R^{2b}$ represents a direct bond, $-Ar^6-$, $-S-Ar^6-$, $-O-Ar^6-$, $-CO-Ar^6-$, $-SO_2-Ar^6-$ or $-C(CF_3)_2-Ar^6-$; $Ar^1$, $Ar^2$, $Ar^{3b}$ and $Ar^6$ each independently represent an arylene group optionally having a substituent; $Ar^{3a}$ and $Ar^4$ each independently represent an aryl group optionally having a substituent; Z represents a direct bond, $-S-$, $-O-$, $-CO-$, $-SO_2-$ or $-C(CF_3)_2-$; and $X^-$ represents an anion.

Advantageous Effects of Invention

The present invention can provide a method which enables to manufacture a polyarylene sulfide resin having a high degree of freedom for designing the constitutional unit and further having a sufficiently high molecular weight. Further, the present invention can provide a poly(arylenesulfonium salt) and a manufacturing method therefor, and a sulfoxide which can be used for the above method.

In the conventional method for synthesizing a polyarylene sulfide resin by homopolymerization of a monofunctional sulfoxide, it is often difficult to control the reaction system. On the other hand, in the method for manufacturing a polyarylene sulfide resin according to the present invention, a reaction of at least two compounds of a sulfoxide and an aromatic compound is utilized. Therefore, it is possible to easily control the reaction system by adjusting formulation of the raw material compounds in the method for manufacturing a polyarylene sulfide resin according to the present invention.

DESCRIPTION OF EMBODIMENTS

Hereinafter, suitable embodiments of the present invention will be described in detail. However, the present invention is never limited to the following embodiments.

The method for manufacturing a polyarylene sulfide resin according to the present embodiment includes: reacting a sulfoxide with an aromatic compound to obtain a poly(arylenesulfonium salt); and dealkylating or dearylating the poly(arylenesulfonium salt) to obtain a polyarylene sulfide resin.

The sulfoxide used in the present embodiment is a compound represented by the following formula (1) and has two sulfinyl groups.

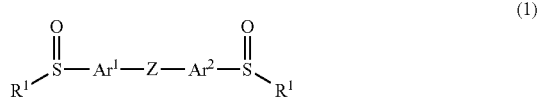
(1)

In formula (1), $R^1$ represents an alkyl group having 1 to 10 carbon atoms or an aryl group optionally having an alkyl group having 1 to 10 carbon atoms; $Ar^1$ and $Ar^2$ each independently represent an arylene group optionally having a substituent; and Z represents a direct bond, $-S-$, $-O-$, $-CO-$, $-SO_2-$ or $-C(CF_3)_2-$. In formula (1), $R^1$ may be an alkyl group having 2 to 10 carbon atoms or an aryl group optionally having an alkyl group having 2 to 10 carbon atoms when Z is $-S-$.

The sulfoxide represented by formula (1) can be obtained, for example, by oxidizing a compound represented by the following formula (3) through a reaction with an oxidant or the like.

$$R^1-S-Ar^1-Z-Ar^2-S-R^1 \tag{3}$$

In formula (3), $R^1$, $Ar^1$, $Ar^2$ and Z are defined in the same manner with $R^1$, $Ar^1$, $Ar^2$ and Z in formula (1), respectively.

The oxidant is not particularly limited and various oxidants can be used. Examples of the oxidant which can be used include potassium permanganate, oxygen, ozone, organic peroxides, hydrogen peroxide, nitric acid, m-chloroperoxybenzoic acid, Oxone (R) and osmium tetroxide.

The compound represented by formula (3) can be obtained, if necessary, by using a compound represented by the following formula (4) and dimethyl disulfide or the like for substituting the halogen atoms each represented by Y with sulfide groups to synthesize a sulfide compound.

$$Y-Ar^1-Z-Ar^2-Y \tag{4}$$

In formula (4), Y represents a halogen atom; and $Ar^1$, $Ar^2$ and Z are defined in the same manner with $Ar^1$, $Ar^2$ and Z in formula (1), respectively. Y is, for example, a chlorine atom, a bromine atom, an iodine atom or the like, and preferably is a chlorine atom.

In the compound represented by formula (1), (3) or (4), $Ar^1$ and $Ar^2$ may be each an arylene group such as phenylene, naphthylene and biphenylene. Although $Ar^1$ and $Ar^2$ can be the same or different, they are preferably the same.

The mode of bonding in $Ar^1$ and $Ar^2$ is not particularly limited, but it is preferably a situation in which bonds are present at positions distant from each other in the arylene group. For example, in the case that $Ar^1$ and $Ar^2$ are each a phenylene group, a unit bonding at the p-position (1,4-phenylene group) and a unit bonding at the m-position (1,3-phenylene group) are preferable, and a unit bonding at the p-position is more preferable. Being composed of a unit bonding at the p-position is preferable in the aspect of the heat resistance and crystalline character of a resin to be obtained.

In the case that the arylene group represented by $Ar^1$ or $Ar^2$ has a substituent, the substituent is preferably an alkyl group having 1 to 10 carbon atoms such as a methyl group, an ethyl group, a propyl group, a butyl group, a pentyl group, a hexyl group, a heptyl group, an octyl group, a nonyl group and a decyl group; a hydroxy group; an amino group; a mercapto group; a carboxyl group; or a sulfo group.

Examples of the compound represented by formula (1) include 4,4'-bis(methylsulfinyl)biphenyl, bis[4-(methylsulfinyl)phenyl]ether, bis[4-(methylsulfinyl)phenyl]sulfide, bis[4-(methylsulfinyl)phenyl]sulfone, bis[4-(methylsulfinyl)phenyl]ketone, 2,2-bis[4-(methylsulfinyl)phenyl]-1,1,1,3,3,3-hexafluoropropane. These compounds can be used singly or in combinations.

Examples of $R^1$ include alkyl groups having 1 to 10 carbon atoms such as a methyl group, an ethyl group, a propyl group, a butyl group, a pentyl group, a hexyl group, a heptyl group, an octyl group, a nonyl group and a decyl group; and aryl groups having a structure of phenyl, naphthyl, biphenyl or the like. Further, the aryl group may have 1 to 4 substituents of an alkyl group having 1 to 10 carbon atoms such as a methyl group, an ethyl group, a propyl group, a butyl group, a pentyl group, a hexyl group, a heptyl group, an octyl group, a nonyl group and a decyl group on the aromatic ring.

The aromatic compound used in the present embodiment is represented by the following formula (2), for example.

$$Ar^{3a}-R^{2a} \tag{2}$$

In formula (2), $R^{2a}$ represents a hydrogen atom, an alkyl group having 1 to 10 carbon atoms, $-Ar^4$, $-S-Ar^4$, $-O-Ar^4$, $-CO-Ar^4$, $-SO_2-Ar^4$ or $-C(CF_3)_2-Ar^4$; and $Ar^{3a}$ and $Ar^4$ each independently represent an aryl group optionally having a substituent. When. $R^{2a}$ is an alkyl group having 1 to 10 carbon atoms, examples thereof include a methyl group, an ethyl group, a propyl group, a butyl group, a pentyl group, a hexyl group, a heptyl group, an octyl group, a nonyl group and a decyl group. When the aryl group represented by $Ar^{3a}$ or $Ar^4$ has a substituent, the substituent is preferably an alkyl group (e.g., a methyl group), a hydroxy group, an amino group, a mercapto group, a carboxyl group or a sulfo group. Examples of $Ar^{3a}$ and $Ar^4$ include aryl groups having a structure of phenyl, naphthyl, biphenyl or the like, and the aryl group may have at least one substituent selected from an alkyl group having 1 to 10 carbon atoms such as a methyl group, an ethyl group, a propyl group, a butyl group, a pentyl group, a hexyl group, a heptyl group, an octyl group, a nonyl group and a decyl group; a hydroxy group; an amino group; a mercapto group; a carboxy group and a sulfo group. Although $Ar^{3a}$ and $Ar^4$ can be the same or different, they are preferably the same.

Examples of the compound represented by formula (2) include benzene, toluene, biphenyl, diphenyl sulfide, diphenyl ether, benzophenone, diphenyl sulfone and hexafluoro-2,2-diphenylpropane. Among these compounds, biphenyl, diphenyl sulfide or diphenyl ether is preferable from the viewpoint of crystalline character. From the viewpoint of obtaining a polyarylene sulfide resin having a higher molecular weight, diphenyl sulfide is preferable. In addition, diphenyl sulfide has a low melting point and can be allowed to function as a solvent in itself and is preferable also from the viewpoint of controlling the reaction temperature or the like. From the viewpoint of lowering the melting point of a polyarylene sulfide resin, diphenyl ether is preferable. From the viewpoint of enhancing the heat resistance of a polyarylene sulfide resin, benzophenone is preferable. From the viewpoint of obtaining an amorphous polyarylene sulfide resin, diphenyl sulfone or hexafluoro-2,2-diphenylpropane is preferable. By making a polyarylene sulfide resin amorphous, it is possible to enhance the molding processability and transparency of the polyarylene sulfide resin.

The reaction of a sulfoxide with an aromatic compound is preferably carried out in the presence of an acid. As the acid, both an organic acid and an inorganic acid can be used. Examples of the acid include non-oxoacids such as hydrochloric acid, hydrobromic acid, hydrocyanic acid and tetrafluoroboric acid; inorganic oxoacids such as sulfuric acid, phosphoric acid, perchloric acid, bromic acid, nitric acid, carbonic acid, boric acid, molybdic acid, isopoly acid and heteropoly acid; partial salts or partial esters of sulfuric acid such as sodium hydrogen sulfate, sodium dihydrogen phosphate, proton-remaining heteropoly acid salts, monomethyl sulfate and trifluoromethane sulfate; mono- or polycarboxylic acids such as formic acid, acetic acid, propionic acid, butanoic acid, succinic acid, benzoic acid and phthalic acid; halogen-substituted carboxylic acids such as monochloroacetic acid, dichloroacetic acid, trichloroacetic acid, monofluoroacetic acid, difluoroacetic acid and trifiuoroacetic acid; mono- or polysulfonic acids such as methanesulfonic acid, ethanesulfonic acid, propanesulfonic acid, benzenesulfonic acid, toluenesulfonic acid, trifluoromethanesulfonic acid and benzenedisulfonic acid; partial metal salts of a poly sulfonic acid such as sodium benzenedisulfonate; and Lewis acids such as antimony pentachloride, aluminum chloride, aluminum bromide, titanium tetrachloride, tin tetrachloride, zinc chloride, copper chloride and iron chloride. Among these acids, it is preferable to use tritluoromethanesulfonic acid or methanesulfonic acid from the viewpoint of reactivity. These acids may be used singly or in combinations of two or more thereof.

In addition, a dehydrating agent may be used in combination because this reaction is a dehydration reaction. Examples of the dehydrating agent include phosphoanhydrides such as phosphorous oxide and phosphorous pentoxide; sulfonic anhydrides such as benzenesulfonic anhydride, methanesulfonic anhydride, trifluoromethanesulfonic anhydride and p-toluenesulfonic anhydride; carboxylic anhydrides such as acetic anhydride, fluoroacetic anhydride and trifluoroacetic anhydride; anhydrous magnesium sulfate, zeolite, silica gel and calcium chloride. These dehydrating agents may be used singly or in combinations of two or more thereof.

A solvent can be appropriately used for the reaction of a sulfoxide with an aromatic compound. Examples of the solvent include alcohol solvents such as methanol, ethanol, propanol and isopropyl alcohol; ketone solvents such as acetone, methyl ethyl ketone and methyl isobutyl ketone; nitrile solvents such as acetonitrile; halogen-containing solvents such as methylene chloride and chloroform; saturated hydrocarbon solvents such as n-hexane, cyclohexane, n-heptane and cycioheptane; amide solvents such as dimethylacetamide and N-methyl-2-pyrrolidone; sulfur-containing solvents such as sulfolane and DMSO; and ether solvents such as tetrahydrofuran and dioxane. These solvents may be used singly or in combinations of two or more thereof.

Conditions for the step of reacting a mixture containing a sulfoxide with an aromatic compound to obtain a poly(arylenesulfonium salt) can be appropriately adjusted so as to allow the reaction to proceed suitably. The reaction temperature is preferably in a range of −30 to 150° C., and more preferably in a range of 0 to 100° C.

The poly(arylenesulfonium salt) obtained in the above step has a constitutional unit represented by the following formula (10).

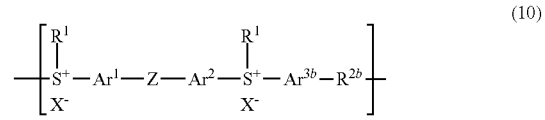

(10)

In formula (10), $R^{2b}$ represents a direct bond, —$Ar^6$—, —S—$Ar^6$—, —O—$Ar^6$—, —CO—$Ar^6$—, —$SO_2$—$Ar^6$— or —$C(CF_3)_2$—$Ar^6$—; $Ar^{3b}$ and $Ar^6$ each independently represent an arylene group optionally having a substituent; $X^-$ represents an anion. $Ar^1$, $Ar^2$, $R^1$ and Z are defined in the same manner with $Ar^1$, $Ar^2$, $R^1$ and Z in formula (1), respectively. $Ar^{3b}$ and $Ar^6$ may be each, for example, an arylene group such as phenylene, naphthylene and biphenylene. Although $Ar^{3b}$ and $Ar^6$ can be the same or different, they are preferably the same. Examples of $X^-$ representing an anion include anions such as sultanate, carboxylate and a halogen ion. In formula (10), Z may be a direct bond, —CO—, —$SO_2$— or —$C(CF_3)_2$— when $Ar^1$, $Ar^2$ and $Ar^{3b}$ are each a 1,4-phenylene group and $R^{2b}$ is a direct bond, and Z may be —S—, —O—, —CO—, —$SO_2$— or —$C(CF_3)_2$— when $Ar^1$, $Ar^2$ and $Ar^{3b}$ are each a 1,4-phenylene group, $R^{2b}$ is —$Ar^6$— and $Ar^6$ is a 1,4-phenylene group.

In the constitutional unit represented by formula. (10), the mode of bonding in $Ar^{3b}$ and $Ar^6$ is not particularly limited, and the same theory can be applied as for the mode of bonding in $Ar^1$ and $Ar^2$ in formula (1), (3), (4).

When the arylene group represented by $Ar^{3b}$ or $Ar^6$ has a substituent, the substituent is preferably an alkyl group having 1 to 10 carbon atoms such as a methyl group, an ethyl group, a propyl group, a butyl group, a pentyl group, a hexyl group, a heptyl group, an octyl group, a nonyl group and a decyl group; a hydroxy group; an amino group; a mercapto group; a carboxyl group; or a sulfo group. However, the fraction of the constitutional unit of formula (10) in which $Ar^1$, $Ar^2$, $Ar^{3b}$ and $Ar^6$ are each an arylene group having a substituent is preferably in a range of 10% by mass or less, and more preferably 5% by mass or less based on the whole poly(arylenesulfonium salt) from the viewpoint of suppressing the reduction of the crystallinity and heat resistance of a polyarylene sulfide resin.

The above constitutional unit which a poly(arylenesulfonium salt) has can be appropriately selected, for example, by changing a combination of a sulfoxide represented by formula (1) and an aromatic compound represented by formula (2) in accordance with a purpose for use of a polyarylene sulfide resin or the like.

The method for manufacturing a polyarylene sulfide resin according to the present embodiment includes dealkylating or dearylating a poly(arylenesulfonium salt). It is believed that dealkylation or dearylation of a poly(arylenesulfonium salt) proceeds as in the following reaction formula, for example.

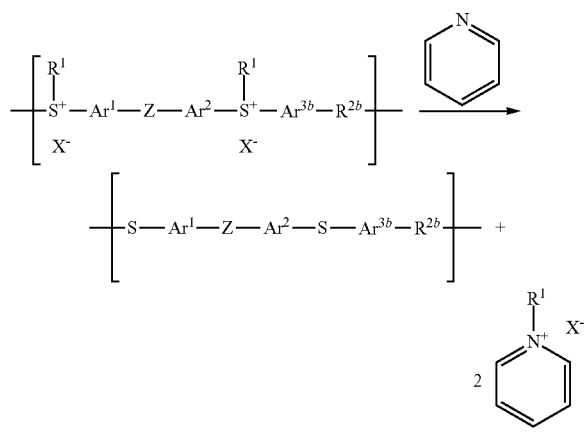

In this step, a dealkylating agent or dearylating agent can be used. The dealkylating agent or dearylating agent includes nucleophiles or reductants. As the nucleophile, a nitrogen-containing aromatic compound, an amine compound, an amide compound or the like can be used. As the reductant, metal potassium, metal sodium, potassium chloride, sodium chloride, hydrazine or the like can be used. These compounds may be used singly or in combinations of two or more thereof.

Examples of the aromatic compound include pyridine, quinoline and aniline. Among these compounds, pyridine, a versatile compound, is preferable.

Examples of the amine compound include trialkylamine and ammonia.

Examples of the amide compound which can be used include aromatic amide compounds and aliphatic amide compounds. An aliphatic amide compound is a compound represented by the following formula (30), for example.

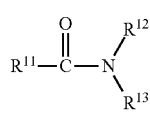

(30)

In formula (30), $R^{11}$, $R^{12}$ and $R^{13}$ each independently represent a hydrogen atom or an alkyl group having 1 to 10 carbon atoms; and $R^{11}$ and $R^{13}$ may be bonded together to form a cyclic structure. Examples of the alkyl group having 1 to 10 carbon atoms include a methyl group, an ethyl group, a propyl group, a butyl group, a pentyl group, a hexyl group, a heptyl group, an octyl group, a nonyl group and a decyl group.

It is believed that the compound represented by formula (30) functions as a dealkylating agent or dearylating agent to dealkylate or dearylate an alkyl group or aryl group bonding to the sulfur atom of a sulfonium salt as illustrated in the following reaction formula, for example.

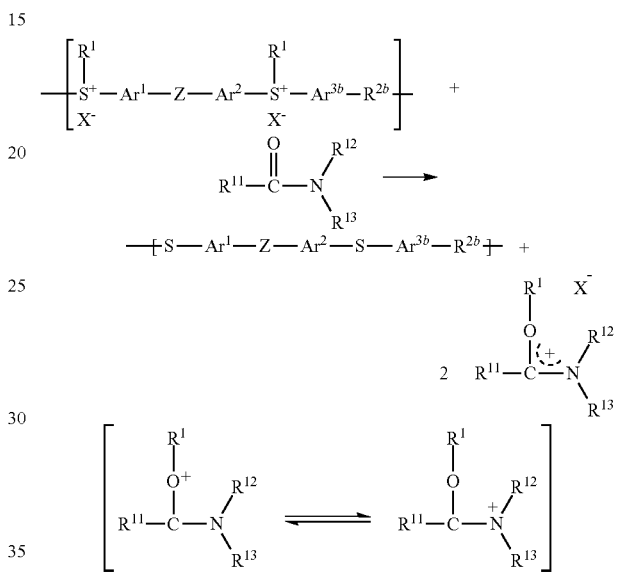

In addition, the aliphatic amide compound has a higher water miscibility than those of aromatic amide compounds and hence can be easily removed by washing the reaction mixture with water. Due to this fact, the amount of an aliphatic amide compound remaining in a polyarylene sulfide resin can be reduced compared with the case that an aromatic amide compound is used.

In this way, it is preferable to use an aliphatic amide compound as an dealkylating agent or dearylating agent because the generation of gas can be suppressed, for example, in processing a resin, which results in quality enhancement of a polyarylene sulfide resin molding and improvement of the working environment, and in addition enhancement of the maintainability of a metal mold. Further, because an aliphatic amide compound is also excellent in solubility for organic compounds, use of the aliphatic amide compound enables to easily remove an oligomer component of a polyarylene sulfide from the reaction mixture. As a result, the oligomer component, which may contribute to the generation of gas, can be removed by the aliphatic amide compound to synergistically enhance the quality of a polyarylene sulfide resin to be obtained.

Examples of the aliphatic amide compound which can be used include primary amide compounds such as formamide; secondary amide compounds such as β-lactam; and tertiary amide compounds such as N-methyl-2-pyrrolidone, dimethylformamide, diethylformamide, dimethylacetamide and tetramethylurea. The aliphatic amide compound preferably includes an aliphatic tertiary amide compound, in which $R^{12}$ and $R^{13}$ are each an aliphatic group, from the viewpoint of solubility for a poly(arylenesulfonium salt) and solubility in water, and N-methyl-2-pyrrolidone is preferable among tertiary amide compounds.

The aliphatic amide compound not only functions as an dealkylating agent or dearylating agent, but also can be used as a reaction solvent because of being excellent in solubility. Although the amount of the aliphatic amide compound to be used is not particularly limited, the lower limit is preferably in a range of 1.00 equivalent or more, more preferably in a range of 1.02 equivalents or more, and still more preferably in a range of 1.05 equivalents or more based on, the total amount of a poly(arylenesulfonium salt). In the case that the amount of the aliphatic amide compound to be used is 1.00 equivalent or more, dealkylation or dearylation of a poly (arylenesulfonium salt) can be carried out satisfactorily. On the other hand, the upper limit is preferably 100 equivalents or less, and more preferably 10 equivalents or less. As the reaction solvent, the aliphatic amide compound may be used alone or in combination, with another solvent such as toluene.

Conditions for the reaction of the poly(arylenesulfonium salt) according to the present embodiment with the aliphatic amide compound can be appropriately adjusted so as to allow dealkylation or dearylation to proceed suitably. The reaction temperature is preferably in a range of 50 to 250° C., and more preferably in a range of 80 to 220° C.

The method for manufacturing a polyarylene sulfide resin according to the present embodiment may further include a step of washing a polyarylene sulfide resin with water, a water-soluble solvent or a mixture solvent thereof. By including such a washing step, it is possible to reliably reduce the amount of a remaining dealkylating agent or dearylating agent contained in a polyarylene sulfide resin to be obtained. This tendency becomes pronounced when an aliphatic amide compound is used as a dealkylating agent or dearylating agent.

By performing a washing step, it is possible to reliably reduce the amount of a dealkylating agent or dearylating agent remaining in a polyarylene sulfide resin to be obtained. The amount of a dealkylating agent or dearylating agent remaining in the resin is preferably in a range of 1000 ppm or less, more preferably in a range of 700 ppm or less, and still more preferably in a range of 100 ppm or less based on the mass of the resin including a polyarylene sulfide resin and other components such as a dealkylating agent or dearylating agent. In the case of 1000 ppm or less, it is possible to reduce a substantial influence on the quality of a polyarylene sulfide resin to be obtained.

The solvent used in the washing step is, although not particularly limited, preferably one which dissolves an unreacted material therein. Examples of the solvent include water; acidic aqueous solutions such as an aqueous solution of hydrochloric acid, an aqueous solution of acetic acid, an aqueous solution of oxalic acid and an aqueous solution of nitric acid; aromatic hydrocarbon solvents such as toluene and xylene; alcohol solvents such as methanol, ethanol, propanol and isopropyl alcohol; ketone solvents such as acetone, methyl ethyl ketone and methyl isobutyl ketone; nitrile solvents such as acetonitrile; ether solvents such as tetrahydrofuran and dioxane; amide solvents such as dimethylacetamide and N-methyl-2-pyrrolidone; and halogen-containing solvents such as dichloromethane and chloroform. These solvents may be used singly or in combinations of two or more thereof. Among these solvents, water and N-methylpyrrolidone are preferable from the viewpoint of removal of the reaction reagents and removal of the oligomer component of the resin.

The polyarylene sulfide resin obtained by the manufacturing method according to the present embodiment has a constitutional unit represented by the following formula (20).

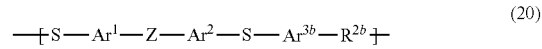

$$-\!\!\left[\!S\!-\!Ar^1\!-\!Z\!-\!Ar^2\!-\!S\!-\!Ar^{3b}\!-\!R^{2b}\right]\!\!-\quad(20)$$

In formula (20), $R^{2b}$, $Ar^1$, $Ar^2$, $Ar^{3b}$ and Z are defined in the same manner with $R^{2b}$, $Ar^1$, $Ar^2$, $A^{3b}$ and Z in formula (10), respectively. In formula (20), Z may be a direct bond, —CO—, —SO$_2$— or —C(CF$_3$)$_2$— when $Ar^1$, $Ar^2$ and $Ar^{3b}$ are each a 1,4-phenylene group and $R^{2b}$ is a direct bond, and Z may be —S—, —O—, —CO—, —SO$_2$— or —C(CF$_3$)$_2$— when $Ar^1$, $Ar^2$ and $Ar^{3b}$ are each a 1,4-phenylene group, $R^{2b}$ is —$Ar^6$— and $Ar^6$ is a 1,4-phenylene group.

In the constitutional unit represented by formula (20), the mode of bonding in $Ar^1$, $Ar^2$, $Ar^{3b}$ and $Ar^6$ is not particularly limited, and the same theory can be applied as for the mode of bonding in $Ar^1$ and $Ar^2$ in formula (1), (3), (4).

When the arylene group represented by $Ar^1$, $Ar^2$, $Ar^{3b}$ and $Ar^6$ has a substituent, the substituent is preferably an alkyl group having 1 to 10 carbon atoms such as a methyl group, an ethyl group, a propyl group, a butyl group, a pentyl group, a hexyl group, a heptyl group, an octyl group, a nonyl group and a decyl group; a hydroxy group; an amino group; a mercapto group; a carboxyl group; or a sulfo group. However, the fraction of the constitutional unit of formula (20) in which $Ar^1$, $Ar^2$, $Ar^3$ and $Ar^6$ are each an arylene group having a substituent is preferably in a range of 10% by mass or less, and more preferably 5% by mass or less based on the whole polyarylene sulfide resin from the viewpoint of suppressing the reduction of the crystallinity and heat resistance of a polyarylene sulfide resin.

The above constitutional unit which a polyarylene sulfide resin has can be appropriately selected, for example, by changing a combination of a sulfoxide represented by formula (1) and an aromatic compound represented by formula (2) in accordance with a purpose for use of a resin or the like.

The weight average molecular weight of the polyarylene sulfide resin obtained by the manufacturing method according to the present embodiment is preferably in a range of 9000 or more, and more preferably 11000 or more. Due to the weight average molecular weight being within such a range, more excellent heat resistance and mechanical properties are exerted. A weight average molecular weight refers to a value measured using gel permeation chromatography. Conditions for measurement using gel permeation chromatography are the same ones as in Examples in the present specification. However, conditions for the measurement can be appropriately changed within a range that does not have a substantial influence on a measurement of a weight average molecular weight.

The melting point of the polyarylene sulfide resin obtained by the manufacturing method according to the present embodiment is preferably in a range of 1.00 to 400° C., and more preferably 150 to 300° C. The melting point of a resin refers to a value measured with a DSC instrument.

The polyarylene sulfide resin obtained by the manufacturing method according to the present embodiment can be combined with another component for utilizing as a polyarylene sulfide resin composition. For example, an inorganic filler can be used as the other component, and a resin other than the polyarylene sulfide resin selected from a thermoplastic resin, an elastomer and a cross-linkable resin or the like can also be used.

Examples of the inorganic filler include powdered fillers such as carbon black, calcium carbonate, silica and titanium oxide; platy fillers such as talk and mica; granular fillers such as a glass bead, a silica bead and a glass balloon; fibrous fillers such as a glass fiber, a carbon fiber and a wollastonite fiber; and a glass flake. These inorganic fillers can be used singly or in combinations of two or more thereof. By formulating an inorganic filler, a composition having a high stiffness and a high thermal stability can be obtained. The polyarylene sulfide resin composition particularly preferably contains at least one inorganic filler selected from the group consisting of a glass fiber, a carbon fiber, carbon black and calcium carbonate.

The content of an inorganic filler is preferably in a range of 1 to 300 parts by mass, more preferably in a range of 5 to 200 parts by mass, and still more preferably in a range of 15 to 150 parts by mass based on 100 parts by mass of the polyarylene sulfide resin. The content of an inorganic filler being within such a range can result in more excellent effect in terms of retaining the mechanical strength of a molding.

The polyarylene sulfide resin composition may contain a resin other than the polyarylene sulfide resin selected from a thermoplastic resin, an elastomer and a cross-linkable resin. These resins can also be formulated in the resin composition together with an inorganic filler.

Examples of the thermoplastic resin to be formulated in the polyarylene sulfide resin composition include polyester, polyamide, polyimide, polyetherimide, polycarbonate, polyphenylene ether, polysulfone, polyether sulfone, polyether ether ketone, polyether ketone, polyethylene, polypropylene, polytetrafluoroethylene, polydifluoroethylene, polystyrene, ABS resins, silicone resins and liquid crystal polymers (e.g., liquid crystal polyester). These thermoplastic resins can be used singly or in combinations of two or more thereof.

Polyamide is a polymer having an amide bond (—NHCO—). Examples of the polyamide resin include (i) polymers obtained by polycondensation of a diamine and a dicarboxylic acid; (ii) polymers obtained by polycondensation of an aminocarboxylic acid; and (iii) polymers obtained by ring-opening polymerization of a lactam.

Examples of the diamine to obtain polyamide include aliphatic diamines, aromatic diamines and alicyclic diamines. As the aliphatic diamine, linear or branched diamines having 3 to 18 carbon atoms are preferable. Examples of a suitable aliphatic diamine include 1,3-trimethylenediamine, 1,4-tetramethylenediamine, 1,5-pentamethylenediamine, 1,6-hexamethylenediamine, 1,7-heptamethylenediamine, 1,8-octamethylenediamine, 2-methyl-1,8-octanediamine, 1,9-nonamethylenediamine, 1,10-decamethylenediamine, 1,11-undecamethylenediamine, 1,12-dodecamethylenediamine, 1,13-tridecamethylenediamine, 1,14-tetradecamethylenediamine, 1,15-pentadecamethylenediamine, 1,16-hexadecamethylenediarnine, 1,17-heptadecamethylenediamine, 1,18-octadecamethylenediamine, 2,2,4-trimethylhexamethylenediamine and 2,4,4-trimethylhexamethylenediamine. These can be used singly or in combinations of two or more thereof.

As the aromatic diamine, diamines having a phenylene group and having 6 to 27 carbon atoms are preferable. Examples of a suitable aromatic diamine include o-phenylenediamine, m-phenylenediamine, p-phenylenediamine, m-xylylenediamine, p-xylylenediamine, 3,4-diaminodiphenyl ether, 4,4'-diaminodiphenyl ether, 4,4'-diaminodiphenylmethane, 3,3'-diaminodiphenyl sulfone, 4,4'-diaminodiphenyl sulfone, 4,4'-diaminodiphenyl sulfide, 4,4'-di(m-aminophenoxy)diphenyl sulfone, 4,4'-di(p-aminophenoxy) diphenyl sulfone, benzidine, 3,3'-diaminobenzophenone, 4,4'-diaminobenzophenone, 2,2-bis(4-aminophenyl)propane, 1,5-diaminonaphthalene, 1,8-diaminonaphthalene, 4,4'-bis(4-aminophenoxy)biphenyl, 2,2-bis[4-(4-aminophenoxy)phenyl]hexafluoropropane, 1,4-bis(4-aminophenoxy) benzene, 1,3-bis(4-aminophenoxy)benzene, 1,3-bis(3-aminophenoxy)benzene, 1,3-bis(3-aminophenoxy)benzene, 4,4'-diamino-3,3'-diethyl-5,5'-dimethyldiphenylmethane, 4,4'-diamino-3,3',5,5'-tetramethyldiphenylmethane, 2,4-diaminotoluene, and 2,2'-dimethylbenzidine. These can be used singly or in combinations of two or more thereof.

As the alicyclic diamine, diamines having a cyclohexylene group and having 4 to 15 carbon atoms are preferable. Examples of a suitable alicyclic diamine include 4,4'-diamino-dicyclohexylenemethane, 4,4'-diamino-dicyclohexylenepropane, 4,4'-diamino-3,3'-dimethyl-dicyclohexylenemethane, 1,4-diaminocyclohexane and piperazine. These can be used singly or in combinations of two or more thereof.

Examples of the dicarboxylic acid to obtain polyamide include aliphatic dicarboxylic acids, aromatic dicarboxylic acids and alicyclic dicarboxylic acids.

As the aliphatic dicarboxylic acid, saturated or unsaturated dicarboxylic acids having 2 to 18 carbon atoms are preferable. Examples of a suitable aliphatic dicarboxylic acid include oxalic acid, malonic acid, succinic acid, glutaric acid, adipic acid, pimelic acid, suberic acid, azelaic acid, sebacic acid, undecanedioic acid, dodecanedioic acid, brassylic acid, tetradecanedioic acid, pentadecanedioic acid, octadecanedioic acid, maleic acid and fumaric acid. These can be used singly or in combinations of two or more thereof.

As the aromatic dicarboxylic acid, dicarboxylic acids having a phenylene group and having 8 to 15 carbon atoms are preferable. Examples of a suitable aromatic dicarboxylic acid include isophthalic acid, terephthalic acid, methylterephthalic acid, biphenyl-2,2'-dicarboxylic acid, biphenyl-4,4'-dicarboxylic acid, diphenylmethane-4,4'-dicarboxylic acid, diphenyl ether-4,4'-dicarboxylic acid, diphenyl sulfone-4,4'-dicarboxylic acid, 2,6-naphthalenedicarboxylic acid, 2,7-naphthalenedic-arboxylic acid and 1,4-naphthalenedicarboxylic acid. These can be used singly or in combinations of two or more thereof. In addition, polycarboxylic acids such as trimellitic acid, trimesic acid and pyromellitic acid can also be used within a range in which melt molding can be performed.

As the aminocarboxylic acid, aminocarboxylic acids having 4 to 18 carbon atoms are preferable. Examples of a suitable aminocarboxylic acid include 4-aminobutyric acid, 6-aminohexanoic acid, 7-aminoheptanoic acid, 8-aminooctanoic acid, 9-aminononanoic acid, 10-aminodecanoic acid, 11-aminoundecanoic acid, 12-aminododecanoic acid, 14-aminotetradecanoic acid, 16-aminohexadecanoic acid and 18-aminooctadecanoic acid. These can be used singly or in combinations of two or more thereof.

Examples of the lactam to obtain polyamide include ε-caprolactam, ω-laurolactam, ζ-enantholactam and η-capryllactam. These can be used singly or in combinations of two or more thereof.

Examples of a preferable combination of the raw materials for polyamide include ε-caprolactam (nylon 6), 1,6-hexamethylenediamine/adipic acid (nylon 6,6), 1,4-tetramethylenediamine/adipic acid (nylon 4,6), 1,6- hexamethylenediamine/terephthalic acid, 1,6-hexamethylenediamine/terephthalic acid/ε-caprolactam, 1,6-hexamethylenediamine/terephthalic acid/adipic acid, 1,9-nonamethylenediamine/terephthalic acid, 1,9-nonamethylenediamine/terephthalic acid/ε-caprolactam, 1,9-nonamethylenediamine/1,6-hexamethylenediamine/terephthalic acid/adipic acid and m-xylylenediamine/adipic acid. Among them, further preferable is a polyamide resin obtained from 1,4-tetramethylenediamine/adipic acid (nylon 4,6), 1,6-hexamethylenediamine/terephthalic acid/ε-caprolactam, 1,6-hexamethylenediamine/terephthalic acid/adipic acid, 1,9-nonamethylenediamine/terephthalic acid, 1,9-nonamethylenediamine/terephthalic acid/ε-caprolactam or 1,9-nonamethylenediamine/1,6-hexamethylenediamine/terephthalic acid/adipic acid.

The content of the thermoplastic resin is preferably in a range of 1 to 300 parts by mass, more preferably in a range of 3 to 100 parts by mass and still more preferably in a range of 5 to 45 parts by mass based on 100 parts by mass of the polyarylene sulfide resin. Due to the content of the thermoplastic resin other than the polyarylene sulfide resin being within such a range, an effect of the further enhancement of heat resistance, chemical resistance and mechanical properties can be obtained.

As the elastomer to be formulated in the polyarylene sulfide resin composition, a thermoplastic elastomer is often used. Examples of the thermoplastic elastomer include polyolefin elastomers, fluorine-based elastomers and silicone elastomers. Note that, in the present specification, thermoplastic elastomers are classified into not the thermoplastic resin, but an elastomer.

In the case that the polyarylene sulfide resin has a functional group such as a carboxyl group, the elastomer (in particular, the thermoplastic elastomer) preferably has a functional group which can react with the functional group of the polyarylene sulfide resin. This enables to obtain a resin composition particularly excellent in adhesion properties, impact resistance and the like. Examples of the functional group include an epoxy group, an amino group, a hydroxyl group, a carboxy group, a mercapto group, an isocyanate group, an oxazoline group and a group represented by the formula: R(CO)O(CO)— or R(CO)O— (wherein R represents an alkyl group having 1 to 8 carbon atoms). A thermoplastic elastomer having the functional group can be obtained, for example, by copolymerization of an α-olefin and a vinyl-polymerizable compound having the functional group. Examples of the α-olefin include α-olefins having 2 to 8 carbon atoms such as ethylene, propylene and butene-1. Examples of the vinyl-polymerizable compound having the functional group include α,β-unsaturated carboxylic acids and alkyl esters such as (meth)acrylic acid and (meth)acrylate thereof; maleic acid, fumaric acid, itaconic acid and other α,β-unsaturated dicarboxylic acids having 4 to 10 carbon atoms and derivatives (mono- or diesters and acid anhydrides thereof) thereof; and glycidyl (meth)acrylate. Among them, ethylene-propylene copolymers and ethylene-butene copolymers having at least one functional group selected from the group consisting of an epoxy group, a carboxy group and a group represented by the formula: R(CO)O(CO)— or R(CO)O— (wherein R represents an alkyl group having 1 to 8 carbon atoms) are preferable in terms of enhancing the toughness and impact resistance.

The content of the elastomer, which varies depending on the type or application and therefore cannot be defined sweepingly, is for example, preferably in a range of 1 to 300 parts by mass, more preferably in a range of 3 to 100 parts by mass, and still more preferably in a range of 5 to 45 parts by mass based on 100 parts by mass of the polyarylene sulfide resin. The content of the elastomer being within such a range can result in an even more excellent effect in terms of ensuring the heat resistance and toughness of a molding.

The cross-linkable resin to be formulated in the polyarylene sulfide resin composition has two or more cross-linkable functional groups. Examples of the cross-linkable functional group include an epoxy group, a phenolic hydroxyl group, an amino group, an amide group, a carboxy group, an acid anhydride group and an isocyanate group. Examples of the cross-linkable resin include epoxy resins, phenol resins and urethane resins.

As the epoxy resin, aromatic epoxy resins are preferable. The aromatic epoxy resin may have a halogen group, a hydroxyl group or the like. Examples of a suitable aromatic epoxy resin include a bisphenol A type epoxy resin, a bisphenol F type epoxy resin, a bisphenol S type epoxy resin, a biphenyl type epoxy resin, a tetramethylbiphenyl type epoxy resin, a phenol novolac type epoxy resin, a cresol novolac type epoxy resin, a bisphenol A novolac type epoxy resin, a triphenylmethane type epoxy resin, a tetraphenylethane type epoxy resin, a dicyclopentadiene-phenol addition reaction type epoxy resin, a phenol aralkyl type epoxy resin, a naphthol novolac type epoxy resin, a naphthol aralkyl type epoxy resin, a naphthol-phenol-cocondensed novolac type epoxy resin, a naphthol-cresol-cocondensed novolac type epoxy resin, an aromatic hydrocarbon formaldehyde resin-modified phenol resin type epoxy resin and biphenyl novolac type epoxy resin. These aromatic epoxy resins can be used singly or in combinations of two or more thereof. Among these aromatic epoxy resins, a novolac type epoxy resin is preferable, and a cresol novolac type epoxy resin is more preferable in terms of an excellent compatibility with other resin components in particular.

The content of the cross-linkable resin is preferably in a range of 1 to 300 parts by mass, more preferably 3 to 100 parts by mass, and still more preferably 5 to 30 parts by mass based on 100 parts by mass of the polyarylene sulfide resin. The content of the cross-linkable resin being within such a range can result in a much more significant effect of enhancing the stiffness and heat resistance of a molding.

The polyarylene sulfide resin composition can contain a silane compound having a functional group. Examples of the silane compound include silane coupling agents such as γ-glycidoxypropyltrimethoxysilane, γ-glycidoxypropyltriethoxysilane, β-(3,4-epoxycyclohexyl)ethyltrimethoxysilane, γ-glycidoxypropyhnethyldiethoxysilane and γ-glycidoxypropylmethyldimethoxysilane.

The content of the silane compound is, for example, in a range of 0.01 to 10 parts by mass, and preferably in a range of 0.1 to 5 parts by mass based on 100 parts by mass of the polyarylene sulfide resin. The content of the silane compound being within such a range can result in an effect of enhancing the compatibility of the polyarylene sulfide resin with other components.

The polyarylene sulfide resin composition may contain a release agent, a colorant, a thermal stabilizer, an ultraviolet stabilizer, a foaming agent, a rust inhibitor, a flame retardant and a lubricant, and an additive other than them. The content of the additive is, for example, in a range of 1 to 10 parts by mass based on 100 parts by mass of the polyarylene sulfide resin.

The polyarylene sulfide resin composition can be obtained in a form of a pelletized compound or the like by a method in which the polyarylene sulfide resin (a reaction product of melt polymerization) and other components are melt-kneaded. The temperature in melt-kneading is, for example, in a range of 250 to 350° C. The duration in melt-kneading is, for example, 5 to 30 seconds. Melt-kneading can be carried out by using a twin-screw extruder or the like.

The polyarylene sulfide resin composition can be processed, alone or in combination with other materials, into a molding excellent in heat resistance, molding processability, dimensional stability or the like by various melt processing methods such as injection molding, extrusion molding, compression molding and blow molding. The polyarylene sulfide resin obtained by the manufacturing method according to the present embodiment or a resin composition containing it enables to manufacture a high-quality molding easily because the amount of gas generated in heating is small.

The polyarylene sulfide resin obtained by the manufacturing method according to the present invention or a resin composition containing the resin possesses various performances such as heat resistance and dimensional stability, which the polyarylene sulfide resin has by nature, and are therefore widely useful for materials for various molding such as injection molding or compression molding for electric/electronic parts such as a connector, a printed substrate and a sealed molding, automotive parts such as a lamp reflector and various electrical component parts, interior decoration materials for various buildings, an airplane, an automobile and the like or precision parts such OA equipment parts, camera parts and clock parts, extrusion molding for a composite, a sheet, a pipe or the like, or pultrusion molding; or materials for a fiber or a film, for example.

EXAMPLES

Hereinafter, the present invention will be described more specifically through exemplifying Examples. However the present invention is never limited to these Examples.

In Examples shown hereinafter, the following reagents were used.

bis[4-(methylthio)phenyl]sulfide: manufactured by Sigma-Aldrich Corporation, product number S203815-25MG nitric acid (1.38): manufactured by Wako Pure Chemical Industries, Ltd., JIS special grade, content 60 to 61%, density 1.38 g/mL diphenyl ether: manufactured by Wako Pure Chemical Industries, Ltd., Wako special grade bromine: manufactured by Wako Pure Chemical Industries, Ltd., JIS special grade n-butyl lithium: manufactured by KANTO CHEMICAL CO., INC., 2.6 mon, n-hexane solution dimethyl disulfide: manufactured by Wako Pure Chemical Industries, Ltd., Wako 1st grade diphenyl sulfide: manufactured by Wako Pure Chemical Industries, Ltd., Wako special grade diphenyl ether: manufactured by Wako Pure Chemical Industries, Ltd., Wako special grade biphenyl: manufactured by Wako Pure Chemical Industries, Ltd., Wako special grade trifluoromethanesulfonic acid: manufactured by Wako Pure Chemical Industries, Ltd., Wako special grade methanesulfonic acid: manufactured by Wako Pure Chemical Industries, Ltd., Wako special grade phosphorus oxide (v) (phosphorous pentoxide): manufactured by Wako Pure Chemical Industries, Ltd., Wako 1st grade 1. Evaluation Method 1-1. Identification Method ($^1$H-NMR)

Measurements were performed with a DPX-400 instrument manufactured by Bruker Corporation after dissolving in various deuterated solvents.

1-2. Identification Method (GC-MS)

Measurements were performed with a GCMS-QP2010 manufactured by Shimadzu Corporation.

1-3.5% Weight Reduction Temperature

Measurements were performed under a nitrogen flow of 20 mL/min at a temperature elevation rate of 20° C./min with a TG-DTA instrument (Rigaku Corporation, TG-8120) to measure respective 5% weight reduction temperatures.

1-4. Melting Point

Measurements were performed to 40 to 350° C. under a nitrogen flow of 50 mL/min under temperature elevation conditions of 20° C./min to determine respective melting points with the DSC instrument Pyris Diamond manufactured by PerkinElmer Co., Ltd.

1-5. Weight Average Molecular Weight

Measurements were performed with the high temperature gel permeation chromatograph. SSC-7000 manufactured by Senshu Scientific co., ltd. The average molecular weight was calculated in terms of a standard polystyrene.

solvent: 1-chloronaphthalene
charge port: 250° C.
temperature: 210° C.
detector: UV detector (360 nm)
sample concentration: 1 g/L
flow rate: 0.7 mL/min 2—Synthesis of Monomer Example 1

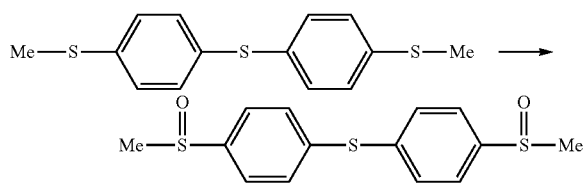

To a 10 L three-necked flask were added 20.0 [g] of bis[4-(methylthio)phenyl]sulfide and 5 [L] of dichloromethane to dissolve and cooled in an ice bath. Thereto 14 [mL] of nitric acid (1.38) was gradually added dropwise, which was stirred at room temperature for 72 hours. The resultant was neutralized with an aqueous solution of potassium carbonate and subjected to an extraction/separation process with dichloromethane, and the organic layer was recovered. The organic layer was dried with anhydrous magnesium sulfate. After filtration, the solvent was removed with a rotary evaporator, and the resultant was dried under a reduced pressure to afford a crude product. Separation was carried out by column chromatography with ethyl acetate as the developing solvent to recover the target product, the solvent was removed with a rotary evaporator, and the resultant was dried under a reduced pressure to afford 6.7 g (yield 30%) of bis[4-(methylsulfinyl)phenyl]sulfide. As a result of $^1$H-NMR measurement and GC-MS measurement, it was confirmed that the target product was obtained.

$^1$H-NMR (solvent: CDCl$_3$): 235, 7.49, 7.61. [ppm]
GC-MS: m/z 310

Example 2

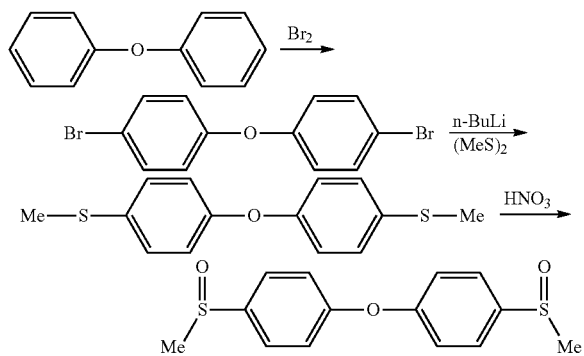

In a 5 L three-necked flask was placed 80.0 [g] of diphenyl ether and dissolved in 2 [L] of dichloromethane as a solvent. After cooling in an ice bath, 129 [mL] of bromine was slowly added dropwise. After the dropwise addition, the resultant was stirred at room temperature for 72 hours. An aqueous solution of sodium hydrogen sulfite was added to the reaction solvent for neutralization to quench the reaction. The organic phase was subjected to an extraction/separation process with dichloromethane to recover the organic layer. Thereafter, the resultant was dried with anhydrous magnesium sulfate. After filtration, the solvent was removed with a rotary evaporator, and then the resultant was dried under a reduced pressure to afford 80.2 [g] (yield 52%) of 4,4'-dibromodiphenyl ether.

$^1$H-NMR (solvent: CDCl$_3$): 6.88, 7.44 [ppm]
GC-MS: m/z 328

In a 3 L three-necked flask was placed 75.0 [g] of the above 4,4'-dibromodiphenyl ether, dissolved by adding 900 [mL] of dry tetrahydrofuran under a nitrogen atmosphere, and cooled to −50° C. Thereto was added 440 [mL] of 2.6 [mol/L] n-butyl lithium solution as a hexane solution and stirred for 30 minutes and then 102 [mL] of dimethyl disulfide was added, which was stirred for 24 hours. An aqueous solution of sodium hydrogen sulfite was added to the reaction mixture to quench the reaction, and the organic layer was extracted with diethyl ether, washed with water and dried with anhydrous magnesium sulfate. After filtration, the solvent was removed with a rotary evaporator, and then the resultant was dried under a reduced pressure to afford 36.0 [g] (yield 60%) of bis[4-(methylthio)phenyl]ether.

$^1$N-NMR (solvent: CDCl$_3$): 2.48, 6.94, 7.26 [ppm]

In a 5 L three-necked flask was placed 20.0 [g] of bis[4-(methylthio)phenyl]ether, dissolved by adding 5 [L] of dichloromethane, and cooled in an ice bath, and thereafter 15 [mL] of nitric acid (1.38) was gradually added dropwise, which was stirred for 72 hours at room temperature. The resultant was neutralized with an aqueous solution of potassium carbonate, subjected to extraction/separation with dichloromethane, and then dried with anhydrous magnesium sulfate. After filtration, the solvent was removed from the filtrate with a rotary evaporator, and the resultant was dried under a reduced pressure to afford a crude product. Separation was carried out by using column chromatography with chloroform/methanol=10/1 (volume ratio) as the developing solvent to recover the target product, and the solvent was removed with a rotary evaporator. The obtained solution was dried under a reduced pressure to afford 9.4 [g] (yield 42%) of bis[4-(methylsulfinyl)phenyl]ether. As a result of $^1$H-NMR measurement and GC-MS measurement, it was confirmed that the target product was obtained. In addition, the absence of the halogen bromine was confirmed by using an SEM-EDS (JEOL Ltd., JSM-6360A).

$^1$H-NMR (solvent: CD$_3$CN): 2.76, 7.18, 7.68 [ppm]
GC-MS: m/z 294

3—Synthesis of Polyarylene Sulfide Resin

Example 3

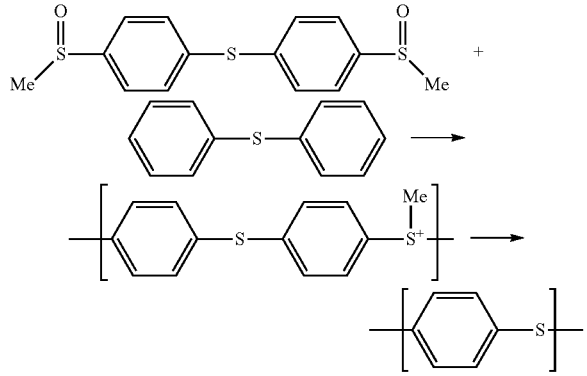

In a 500 mL separable flask was placed 0.932 [g] of bis[4-(methylsulfinyl)phenyl]sulfide, and 0.560 [g] of diphenyl sulfide was added under a nitrogen atmosphere, and after cooling in an ice bath 5 [mL] of trifluoromethanesulfonic acid was slowly added dropwise. The temperature was raised to a room temperature followed by stirring for 20 hours. The reaction solution was poured into water, stirred for 10 minutes, filtered, and thereafter washed with water followed by filtration to recover a solid. The solvent was removed with a rotary evaporator, and the resultant was dried under a reduced pressure to afford 2.25 [g] (yield 99%) of poly[methyl trifluoromethanesulfonate(4-phenylthiophenyl)sulfonium].

A small amount of the sample was collected for analysis, and after being ion-exchanged with an excessive amount of methanesulfonic acid, dissolved in deuterated DMSO, which was subjected to $^1$H-NMR measurement and as a result it was confirmed that the target product was synthesized.

$^1$H-NMR (solvent: deuterated DMSO): 3.27, 3.93, 7.76, 8.19 [ppm]

In a 100 mL eggplant flask was placed 2.00 [g] of poly[methyl trifluoromethanesulfonate(4-phenylthiophenyl)sulfonium], and 100 [mL] of pyridine was added, which was stirred at room temperature for 30 minutes followed by raising the temperature to 110° C. and stirring for 20 hours. After cooling to a room temperature, the reaction solution was placed into water, and the precipitate was filtered out by filtration and washed with chloroform, NMP and water. After washing, the solid was dried under a reduced pressure to afford 0.64 [g] (yield 56%) of polyphenylene sulfide. The weight average molecular weight was 20000, the melting point was 278° C., and the 5% weight reduction temperature was 478° C.

Example 4

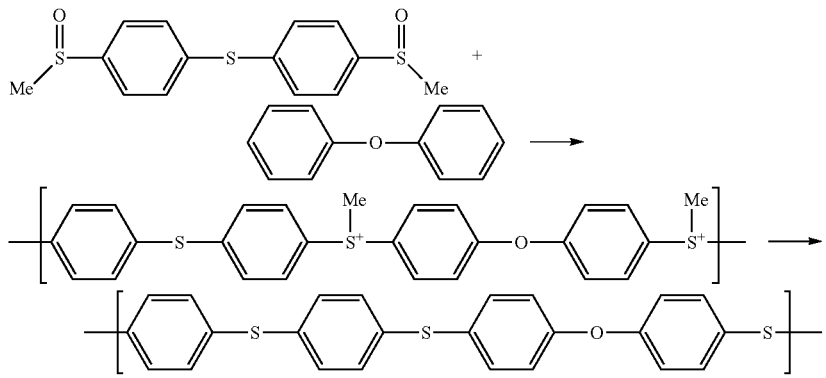

In the same way as in Example 3 except that 0.511 [g] of diphenyl ether was used in place of diphenyl sulfide, 2.19 [g] (yield 98%) of poly[methyl trifluoromethanesulfonate(4-phenyloxyphenyl)sulfonium-4'-methyl(4-phenylthiophenyl)sulfonium] was obtained.

A small amount of the sample was collected for analysis, and after being ion-exchanged with an excessive amount of methanesulfonic acid, dissolved in deuterated acetic acid, which was subjected to 1H-NMR measurement and as a result it was confirmed that the target product was synthesized.

$^1$H-NMR (solvent: deuterated acetic acid): 3.17, 3.92, 7.61, 7.87, 8.08, 8.18 [ppm]

In a 100 mL eggplant flask was placed 2.00 [g] of poly[methyl trifluoromethanesulfonate(4-phenyloxyphenyl)sulfonium-4'-methyl(4-phenylthiophenyl)sulfonium], and 100 [mL] of pyridine was added, which was stirred at room temperature for 30 minutes followed by raising the temperature to 110° C. and stirring for 20 hours. After cooling to a room temperature, the reaction solution was placed into water, and the precipitate was filtered out by filtration and washed with chloroform, NMP and water. After washing, the solid was dried under a reduced pressure to afford 0.54 [g] (yield 48%) of poly[(phenylene ether)-(phenylene sulfide)]. The weight average molecular weight was 12000, the melting point was 229° C., and the 5% weight reduction temperature was 491° C.

Example 5

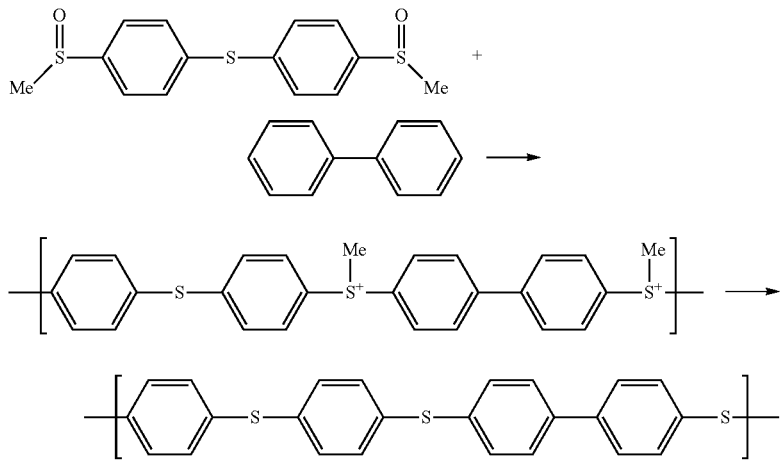

In the same way as in Example 3 except that 0.463 [g] of biphenyl was used in place of diphenyl sulfide, 2.08 [g] (yield 95%) of poly[methyl trifluoromethanesulfonate(4-phenylthiophenyl)sulfonium-4'-methyl(4-bi phenyl)sulfonium] was obtained.

A small amount of the sample was collected for analysis, and after being ion-exchanged with an excessive amount of methanesulfonic acid, dissolved in deuterated acetonitrile, which was subjected to $^1$H-NMR measurement and as a result it was confirmed that the target product was synthesized.

1H-NMR (deuterated acetonitrile): 3.32, 3.58, 7.45, 7.66, 7.78, 7.95 [ppm]

In a 100 mL, eggplant flask was placed 1.80 [g] of poly[methyl trifuoromethanesulfonate(4-phenylthiophenyl)sulfonium-4'-methyl(4-bi phenyl)sulfonium], and 100 [mL] of pyridine was added, which was stirred at room temperature for 30 minutes followed by raising the temperature to 110° C. and stirring for 20 hours. After cooling to a room temperature, the reaction solution was placed into water, and the precipitate was filtered out by filtration and washed with chloroform, NMP and water. After washing, the solid was dried under a reduced pressure to afford 0.87 [g] (yield 88%) of poly[(phenylene sulfide)-(biphenylene sulfide)]. The weight average molecular weight was 18000, the melting point was 325° C., and the 5% weight reduction temperature was 505° C.

Example 6

In the same way as in Example 3 except that 5 [mL] of methanesulfonic acid and 1 [g] of phosphorus oxide were used in place of trifluoromethanesulfonic acid, 1.76 [g] (yield 90%) of poly[methyl methanesulfonate(4-phenylthiophenyl)sulfonium] was obtained.

A small amount of the sample was collected for analysis, and dissolved in deuterated DMSO, which was subjected to $^1$H-NMR measurement and as a result it was confirmed that the target product was synthesized.

$^1$H-NMR (deuterated DMSO): 3.27, 3.93, 7.76, 8.19 [ppm]

In a 100 mL eggplant flask was placed 1.50 [g] of poly[methyl methanesulfonate(4-phenylthiophenyl)sulfonium], and 100 [mL] of pyridine was added, which was stirred at room temperature for 30 minutes followed by raising the temperature to 110° C. and stirring for 72 hours. After cooling to a room temperature, the reaction solution was placed into water, and the precipitate was filtered out by filtration and washed with chloroform, NMP and water. After washing, the solid was dried under a reduced pressure to afford 0.60 [g] (yield 60%) of polyphenylene sulfide. The weight average molecular weight was 60000, the melting point was 278° C., and the 5% weight reduction temperature was 478° C.

Example 7

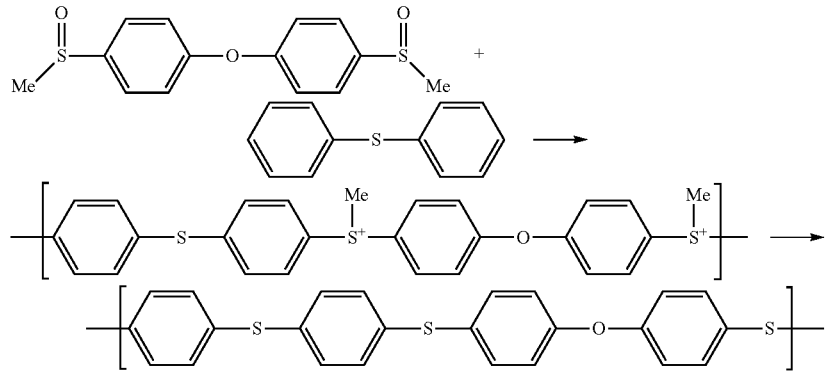

In the same way as in Example 3 except that 0.885 [g] of bis[4-(methylsulfinyl)phenyl]ether was used in place of bis[4-(methylsulfinyl)phenyl]sulfide, 2.15 [g] (yield 95%) of poly[methyl trifluoromethanesulfonate(4-phenyloxyphenyl)sulfonium-4'-methyl(4-phenylthiophenyl)sulfonium] was obtained.

A small amount of the sample was collected for analysis, and after being ion-exchanged by placing it into an excessive amount of methanesulfonic acid, dissolved in deuterated acetic acid, which was subjected to $^1$H-NMR measurement and as a result it was confirmed that the target product was synthesized.

$^1$H-NMR. (solvent: deuterated acetic acid): 3.17, 3.92, 7.61, 7.87, 8.08, 8.18 [ppm]

In a 100 mL eggplant flask was placed 2.0 [g] of poly[methyl trifluoromethanesulfonate(4-phenyloxyphenyl)sulfonium-4'-methyl(4-phenylthiophenyl)sulfonium], and 100 [mL] of pyridine was added, which was stirred at room temperature for 30 minutes followed by raising the temperature to 110° C. and stirring for 20 hours. After cooling to a room temperature, the reaction solution was placed into water, and the precipitate was filtered out by filtration and washed with chloroform, NMP and water. After washing, the solid was dried under a reduced pressure to afford 0.50 [g] (yield 45%) of poly[(phenylene ether)-(phenylene sulfide)]. The weight average molecular weight was 18000, the melting point was 225° C., and the 5% weight reduction temperature was 489° C.

Example 8

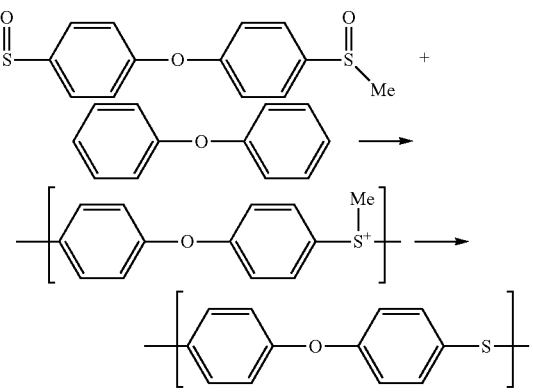

In the same way as in Example 3 except that 0.885 [g] of bis[4-(methylsulfinyl)phenyl]ether and 0.511 [g] of diphenyl ether were used in place of bis[4-(methylsulfinyl)phenyl]sulfide and diphenyl sulfide, 2.15 [g] (yield 98%) of poly[methyl trifluoromethanesulfonate(4-phenyloxyphenyl)sulfonium] was obtained.

A small amount of the sample was collected for analysis, and after being ion-exchanged by placing it into an excessive amount of methanesulfonic acid, dissolved in deuterated acetonitrile, which was subjected to $^1$H-NMR measurement and as a result it was confirmed that the target product was synthesized.

$^1$H-NMR (solvent: CD$_3$CN): 3.33, 3.58, 7.36, 7.94 [ppm]

In a 100 mL eggplant flask was placed 2.0 [g] of poly[methyl trifluoromethanesulfonate(4-phenyloxyphenyl)sulfonium], and 100 [mL] of pyridine was added, which was stirred at room temperature for 30 minutes followed by raising the temperature to 110° C. and stirring for 20 hours. After cooling to a room temperature, the reaction solution was placed into water, and the precipitate was filtered out by filtration and washed with chloroform, NMP and water.

After washing, the solid was dried under a reduced pressure to afford 0.44 [g] (yield 40%) of poly[(phenylene ether)-(phenylene sulfide)]. The weight average molecular weight was 22000, the melting point was 190° C., and the 5% weight reduction temperature was 515° C.

Comparative Example 1

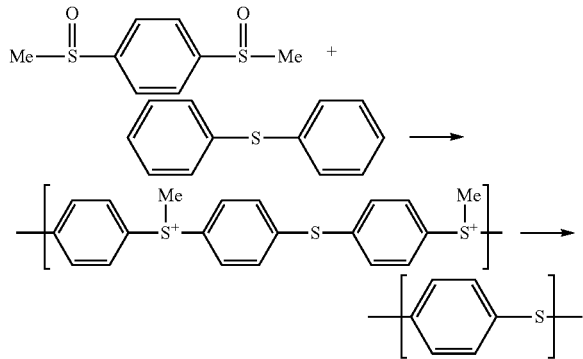

In a 500 mL separable flask was placed 2.00 [g] of 1,4-bis(methylsulfinyl)benzene, and 1.84 [g] of diphenyl sulfide and 3.0 [g] of phosphorous pentoxide were added under a nitrogen atmosphere, which was cooled in an ice bath. Thereafter, 30 [mL] of trifluoromethanesulfonic acid was slowly added dropwise. After adding dropwise at 0° C. for 1 hour, the resultant was stirred at room temperature for 24 hours. Diethyl ether was added to the reaction solution, which was filtrated to afford 5.5 [g] (yield 85%) of poly[methylsulfonio-1,4-phenylenemethylsulfonio-1,4-phenyleneoxy-1,4-phenylene bistriflate].

A small amount of the sample was collected for analysis, and after being ion-exchanged with an excessive amount of methanesulfonic acid, dissolved in deuterated DMSO, which was subjected to $^1$H-NMR measurement and as a result it was confirmed that the target product was synthesized.

$^1$H-NMR (deuterated DMSO): 3.27, 3.83, 7.83, 8.35 [ppm]

In a 500 mL eggplant flask was placed 5.0 [g] of poly[methylsulfonio-1,4-phenylenemethylsulfonio-1,4-phenyleneoxy-1,4-phenylene bistriflate], and 200 mL of pyridine was added followed by raising the temperature to 110° C. and stirring for 2 hours. After cooling to a room temperature, the reaction solution was placed into water, and washed with hydrochloric acid and washed with water. After washing, the solid was dried under a reduced pressure to afford 1.7 [g] (yield 70%) of polyphenylene sulfide. The weight average molecular weight was 8000, the melting point was 278° C., and the 5% weight reduction temperature was 450° C.

It was confirmed that the sulfoxide compounds synthesized in Examples 1, 2, respectively, could be used for the method for manufacturing a polyarylene sulfide resin. It was confirmed that polyarylene sulfide resins having various structural units could be manufactured by changing a combination of a sulfoxide and an aromatic compound as in Examples 3 to 8. In addition, it was confirmed that, according to the manufacturing methods in Examples 3 to 8, a polyarylene sulfide resin could be manufactured which has a higher molecular weight than that in the case of the manufacturing method in Comparative Example 1.

The invention claimed is:

1. A polyarylene sulfide resin having a constitutional unit represented by the following formula (20):

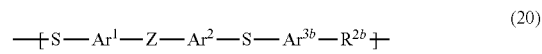 (20)

wherein
R$^{2b}$ represents —Ar$^6$— or —C(CF$_3$)$_2$—Ar$^6$—;
Ar$^1$, Ar$^2$, and Ar$^{3b}$ each independently represent a phenylene group or a naphthylene group;
Ar$^6$ represents an arylene group optionally having a substituent; and
Z represents a direct bond, —S—, —O—, or —C(CF$_3$)$_2$—;
wherein
Z is —O—, or —C(CF$_3$)$_2$— when Ar$^1$, Ar$^2$ and Ar$^{3b}$ are each a 1,4-phenylene group, R$^{2b}$ is —Ar$^6$— and Ar$^6$ is a 1,4-phenylene group.

2. The polyarylene sulfide resin of claim 1, wherein the melting point of the polyarylene sulfide resin is in a range of 100 to 400° C.

3. A polyarylene sulfide resin having a constitutional unit represented by the following formula (20):

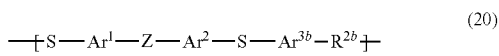 (20)

wherein
R$^{2b}$ represents a direct bond, —Ar—, or —C(CF$_3$)$_2$—Ar$^6$—;
Ar$^1$, Ar$^2$, and Ar$^{3b}$ each independently represent a phenylene group or a naphthylene group;
Ar$^6$ represents an arylene group optionally having a substituent;
Z represents —S—, —O—, or —C(CF$_3$)$_2$—;
wherein
Z is —C(CF$_3$)$_2$— when Ar$^1$, Ar$^2$ and Ar$^{3b}$ are each a 1,4-phenylene group and R$^{2b}$ is a direct bond; and
Z is —O—, or —C(CF$_3$)$_2$— when Ar$^1$, Ar$^2$ and Ar$^{3b}$ are each a 1,4-phenylene group, R$^{2b}$ is —Ar$^6$— and Ar$^6$ is a 1,4-phenylene group.

4. The polyarylene sulfide resin of claim 3, wherein the melting point of the polyarylene sulfide resin is in a range of 100 to 400° C.

* * * * *